United States Patent
Usvyat et al.

(10) Patent No.: US 12,315,530 B2
(45) Date of Patent: May 27, 2025

(54) SYSTEMS AND METHODS FOR GENERATING ANONYMIZED ACOUSTIC FINGERPRINTS

(71) Applicant: Fresenius Medical Care Holdings, Inc., Waltham, MA (US)

(72) Inventors: Len Usvyat, Boston, MA (US); Thomas Charles Blanchard, Somerville, MA (US); Sheetal Chaudhuri, Arlington, MA (US); Wendy Millette, Concord, MA (US); Franklin W. Maddux, Lincoln, MA (US); Caitlin Kelly Monaghan, Arlington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1156 days.

(21) Appl. No.: 16/748,115

(22) Filed: Jan. 21, 2020

(65) Prior Publication Data
US 2020/0234818 A1  Jul. 23, 2020

Related U.S. Application Data

(60) Provisional application No. 62/867,402, filed on Jun. 27, 2019, provisional application No. 62/795,469, filed on Jan. 22, 2019.

(51) Int. Cl.
*G10L 25/51* (2013.01)
*A61B 7/04* (2006.01)
(Continued)

(52) U.S. Cl.
CPC ............. *G10L 25/51* (2013.01); *A61B 7/04* (2013.01); *G01H 17/00* (2013.01); *G06F 21/6245* (2013.01)

(58) Field of Classification Search
CPC ....... G10L 25/51; G06F 21/6245; A61B 7/04; G01H 17/00
See application file for complete search history.

(56) References Cited

U.S. PATENT DOCUMENTS 11,864,880 B2 * 1/2024 Abeyratne ............. A61B 5/411
12,070,323 B2 * 8/2024 Chou ...................... G06N 20/00
(Continued)

FOREIGN PATENT DOCUMENTS

CN 1870935 A 11/2006
CN 101732074 A 6/2010
(Continued)

OTHER PUBLICATIONS

International Preliminary Report on Patentability in International Appln. No. PCT/US2020/014381, dated Aug. 5, 2021, 10 pages.
(Continued)

*Primary Examiner* — Joseph Saunders, Jr.
*Assistant Examiner* — Joseph Saunders
(74) *Attorney, Agent, or Firm* — Fish & Richardson P.C.

(57) ABSTRACT

Systems and methods for generating anonymized acoustic fingerprints. For a predetermined time interval, raw audio data associated with an environment can be captured and processed. Based on the captured raw audio data, a plurality of discrete data elements can be generated.

24 Claims, 4 Drawing Sheets

(51) Int. Cl.
    *G01H 17/00*     (2006.01)
    *G06F 21/62*     (2013.01)

(56) References Cited

U.S. PATENT DOCUMENTS

| | | | |
|---|---|---|---|
| 2009/0082676 A1* | 3/2009 | Bennison | A61M 1/3656 |
| | | | 600/462 |
| 2009/0247869 A1 | 10/2009 | Rambod et al. | |
| 2011/0125063 A1* | 5/2011 | Shalon | A61B 5/4205 |
| | | | 600/590 |
| 2014/0275856 A1 | 9/2014 | Kohlrausch et al. | |
| 2015/0073306 A1* | 3/2015 | Abeyratne | G16H 50/30 |
| | | | 600/586 |
| 2016/0179466 A1 | 6/2016 | Weiss et al. | |
| 2016/0283681 A1* | 9/2016 | Falck | G16H 40/63 |
| 2017/0173262 A1* | 6/2017 | Veltz | G16H 20/17 |
| 2018/0075203 A1* | 3/2018 | West | G16H 40/40 |
| 2018/0357380 A1* | 12/2018 | Wang | G06T 7/70 |

FOREIGN PATENT DOCUMENTS

| | | | |
|---|---|---|---|
| CN | 102078202 A | 6/2011 | |
| CN | 105872011 A | 8/2016 | |

OTHER PUBLICATIONS

Mielke et al. "An assistive technology for hearing-impaired persons: Analysis, requirements and architecture," Engineering in Medicine and Biology Society (EMBC), 35th Annual International Conference of the IEEE, Jul. 3-7, 2013, Osaka, Japan, 4702-4705.

Sainburg, "Tim Sainburg—Spectograms, MFCCs, and Inversion in Python," Jul. 7, 2018, retrieved on May 4, 2023, retrieved from URL <https://timsainburg.com/python-mel-compression-inversion.html>, 15 pages.

International Search Report and Written Opinion in Application No. PCT/US2020/014381, dated Mar. 23, 2020, 15 pages.

Melani Irene Plett, "Ultra arterial vibrometry with wavelet-based detection and estimation", Doctoral dissertation, 247 pages 2000.

Cano et al., "A Review of Audio Fingerprinting," The Journal of VLSI Signal Processing, Nov. 2005, 41:271-284.

Usvyat et al., "Seeing Through Sound: Acoustic Fingerprinting," Sep. 3, 2019, retrieved from URL <https://fmcna.com/insights/amr/2019/seeing-through-sound--acoustic-fingerprinting/>, 18 pages.

Beltran et al., "Recognition of audible disruptive behavior from people with dementia," Personal and Ubiquitous Computing, Dec. 2018, 23(1):145-157.

* cited by examiner

SYSTEMS AND METHODS FOR GENERATING ANONYMIZED ACOUSTIC FINGERPRINTS

CLAIM OF PRIORITY

This application claims priority under 35 USC § 119(e) to U.S. Patent Application Ser. No. 62/867,402, filed on Jun. 27, 2019, and U.S. Patent Application Ser. No. 62/795,469, filed on Jan. 22, 2019, the entire contents of which are hereby incorporated by reference.

TECHNICAL FIELD

This disclosure generally relates to acoustic fingerprints. In particular, this disclosure relates to systems and methods for generating anonymized acoustic fingerprints, for example, in medical facilities or other kinds of environments.

BACKGROUND

An acoustic fingerprint is a condensed digital summary that can be deterministically generated from an audio signal. Acoustic fingerprints can be used to identify an audio sample and/or quickly locate similar items in a database. Some conventional uses of acoustic fingerprinting include identifying songs, identifying advertisements, sound effect library management, and video file identification. Typical acoustic fingerprinting algorithms take into account the perceptual characteristics of the audio. For example, perceptual characteristics often exploited by conventional acoustic fingerprinting techniques include an average zero crossing rate, estimated tempo, average spectrum, spectral flatness, prominent tones across a set of frequency bands, and bandwidth. These characteristics are generally found in the continuous frequency domain.

SUMMARY

In at least one aspect of the present disclosure a method of generating an anonymized acoustic fingerprint for an environment is provided. The method includes capturing, using at least one acoustic sensor, raw sound data associated with the environment during a predetermined time interval. The method includes receiving the raw sound data associated with the predetermined time interval. The method includes generating, based on the received raw sound data, a plurality of discrete data elements. The method includes storing, in memory, the plurality of discrete data elements for the predetermined time interval.

The plurality of discrete data elements can include at least one of: an intensity value, a centroid value, a spread value, a skewness value, a kurtosis value, a decrease value, or a mel-frequency cepstral coefficient. The predetermined time interval can be greater than 5 seconds. The raw sound data can include sound generated by at least one of: a heart or arteriovenous fistula thrill.

The method can include predicting, based on the plurality of discrete data elements, one or more performance outcomes associated with the environment. The method can include identifying a pattern of the plurality of discrete data elements and determining, based on the identified pattern, at least one characteristic of the environment.

In at least one other aspect of the present disclosure, a system is provided. The system includes at least one acoustic sensor configured to capture raw sound data associated with an environment, a computer-readable medium including computer-executable instructions, and one or more processors configured to execute the computer-executable instructions. When the one or more processors are executing the computer-executable, the one or more processors are configured to carry out operations to receive, from the at least one acoustic sensor, raw sound data associated with an environment during a predetermined time interval, generate, based on the received raw sound data, a plurality of discrete data elements, store, in memory, the plurality of discrete data elements for the predetermined time interval.

The plurality of discrete data elements can include at least one of: a volume element, a centroid element, a spread element, a skewness element, a kurtosis element, a decrease element, or a mel-frequency cepstral coefficient. The predetermined time interval can greater than 5 seconds. The acoustic sensor can be a microphone. The raw sound data can include sound generated by at least one of: a heart or arteriovenous fistula thrill.

When the one or more processors are executing the computer-executable, the one or more processors can be configured to carry out operations to predict, based on the plurality of discrete data elements, one or more performance outcomes associated with the environment.

These and other aspects, features, and implementations can be expressed as methods, apparatus, systems, components, program products, methods of doing business, means or steps for performing a function, and in other ways, and will become apparent from the following descriptions, including the claims.

Implementations can include one or more of the following advantages. Sound data representing acoustic noise in an environment (e.g., clinical setting, restaurant setting, government setting, etc.) can be captured and processed during a predetermined time interval (e.g., 10 seconds, 1 minute, etc.), and then processed and summarized in the form of an acoustic fingerprint of the environment. Processing the sound data can include converting the sound data into a plurality of discrete data elements that completely anonymizes the sound data. Among other advantages, these techniques enable the transformation of sound collected in a setting, where maintaining personal privacy may be important, into data that cannot be converted back into identifiable sounds. The collection of data can be used in efforts to associate sound and performance outcomes without breaching the privacy of personnel within the environment. Thus, when compared to conventional audio fingerprint processing technology, the techniques described herein can allow for, among other things, improved data security and privacy when capturing an acoustic fingerprint of an environment.

These and other aspects, features, and implementations can be expressed as methods, apparatus, systems, components, program products such as computer-readable storage mediums, means or steps for performing a function, and in other ways.

These and other aspects, features, and implementations will become apparent from the following descriptions, including the claims.

DETAILED DESCRIPTION

Conventional acoustic fingerprinting technology typically involves capturing an audio sample of an environment and identifying certain continuous elements within the audio sample. However, when capturing the audio sample, certain information that may be considered private and/or sensitive may be recorded and stored. Thus, conventional acoustic fingerprinting technology might not be suitable for environments in which maintaining privacy is important, such as medical facilities and government buildings.

The present disclosure provides systems and methods for generating anonymized acoustic fingerprints of an environment. Raw sound data is captured in an environment for a predetermined time interval. The raw sound data is used to generate a plurality of discrete data elements for the predetermined time interval. By converting the raw sound data to discrete data elements, a unique audio signature of an environment can be generated without storing any discernable audio information.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not provide any of the advantages discussed above or might only provide one of the advantages discussed above. Although headings are provided, data related to a particular heading, but not found in the section having that heading, may also be found elsewhere in this description.

Figure 1:
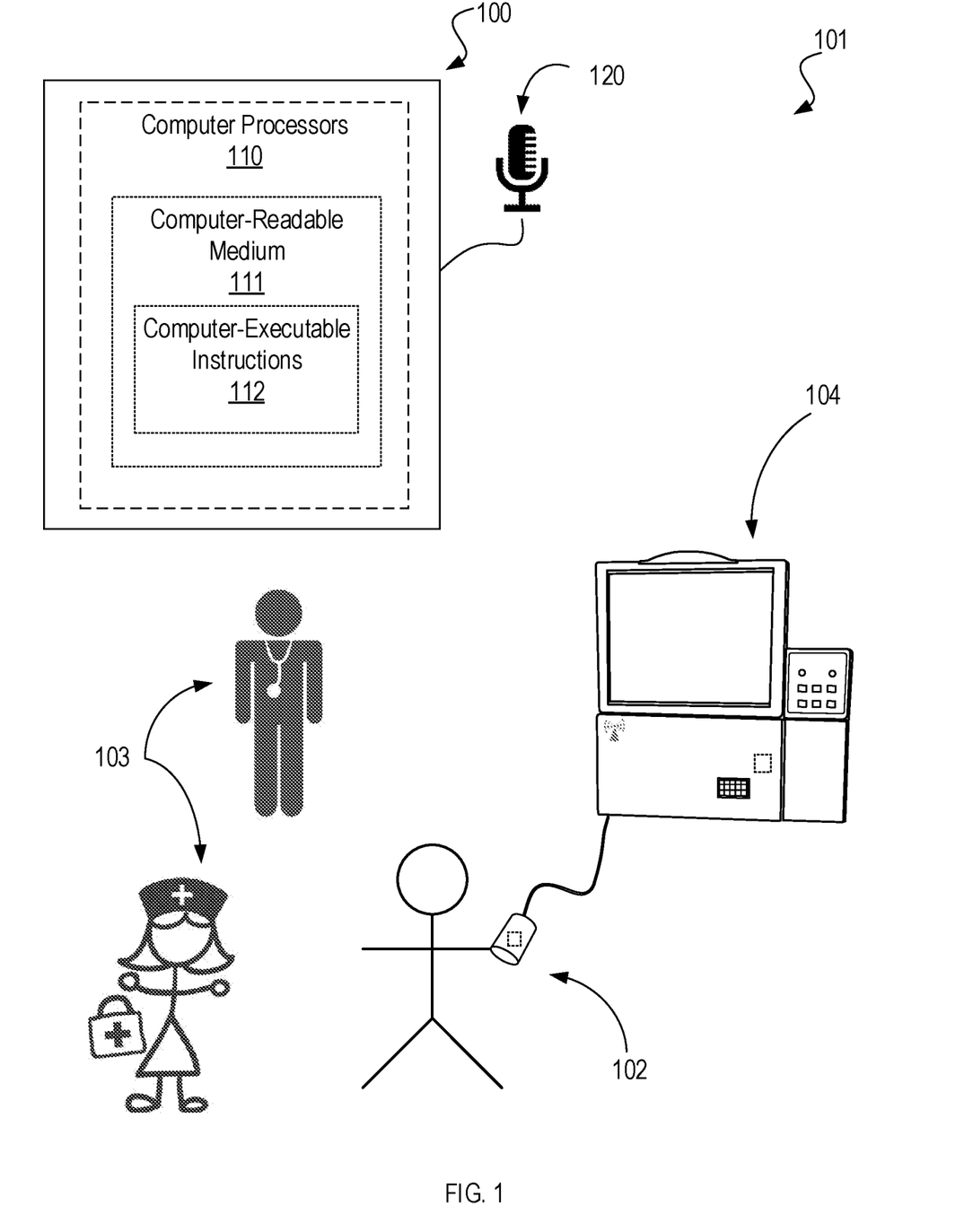
FIG. 1 shows an environment including a system for generating an anonymized acoustic fingerprint for the environment.

FIG. 1 shows an environment 101 including a system 100 for generating an anonymized acoustic fingerprint for the environment 101. The environment 101 is a medical environment. The environment 101 includes medical personnel 103 and a patient 102 receiving treatment from a dialysis machine 104. The system 100 includes one or more computer processors 110 and one or more acoustic sensors 120. The computer processors 110 include a computer-readable medium 111. The computer-readable medium 111 includes computer-executable instructions 112.

The one or more acoustic sensors 120 are communicatively coupled to the computer processors 110. The one or more acoustic sensors 120 are configured to measure ambient noise and provide audio data to the computer processors 110. For example, the one or more acoustic sensors 120 can capture audio data from interactions between the medical personnel 103 and the patient 102. As another example, the one or more acoustic sensors 120 can capture audio data associated with the dialysis machine 104, such as audible alerts and operational noises. Although shown as only including one acoustic sensor 120, the system 100 can include more acoustic sensors 120. For example, the system 100 can include two acoustic sensors 120, four acoustic sensors 120, eight acoustic sensors 120, and so forth. The one or more acoustic sensors 120 are microphones that convert sound into an electrical signal. Each microphone can be one of several types of microphones. In some implementations, the one or more acoustic sensors 120 include a moving-coil (e.g., dynamic) microphone. In some implementations, the one or more acoustic sensors 120 includes a ribbon microphone. The one or more acoustic sensors 120 can also include a carbon microphone, a piezo microphone, a fiber optic microphone, a laser microphone, and/or a microelectromechanical microphone. In some implementations, at least one of the one or more acoustic sensors 120 include a preamplifier, which can convert a relatively weak electrical signal into a stronger signal output such that the output signal is noise-tolerant and strong enough for further processing. Each of the one or more acoustic sensors 120 can be located proximate to the computer processors 110 or remote from the computer processors 110. For example, the acoustic sensors 120 can be located in a same room of a building as the computer processors 110. In some implementations, at least some of the one or more acoustic sensors 120 are located in different rooms of a building from the computer processors 110. In some implementations, at least some of the one or more acoustic sensors 120 are located in a different building than the computer processors 110.

The computer-readable medium 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 111 includes code-segment having executable instructions.

The computer processors 110 are communicatively coupled to the one or more acoustic sensors 120. In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

When the computer processors 110 execute the computer-executable instructions 112, the computer processors 110 carry out one or more operations. In some implementations, when the computer processors 110 execute the computer-executable instructions 112, the computer processors 110 are configured to receive, from the one or more acoustic sensors 120, raw sound data associated with the environment in which the one or more acoustic sensors 120 are located. For example, the one or more acoustic sensors 120 can capture soundwaves, convert the soundwaves into raw usable data (e.g., electronic energy), amplify the raw usable data with a preamplifier, and send the amplified raw usable data to the computer processors 110. In some implementations, the one or more acoustic sensors 120 are caused by the computer processors 110 to begin capturing the raw sound data for a predetermined time interval, where the computer processors 110 cause the one or more acoustic sensors to stop capturing raw sound data at the end of the predetermined time interval (e.g., an audio sample/time series). In some implementations, the predetermined time interval is greater than 5 seconds. In some implementations, the predetermined time interval is greater than 10 seconds. The predetermine time interval can be user selected and/or a manufacturing design choice and be based on computational power, efficiency, and data storage considerations.

When the computer processors 110 execute the computer-executable instructions 112, the computer processors 110 are configured to generate, based on the received raw sound data, a plurality of discrete data elements. In some implementations, the plurality of discrete data elements includes a plurality of Mel-frequency cepstral coefficients. Mel-frequency cepstral coefficients (MFCC) collectively make up a mel-frequency cepstrum (MFC). A MFC is a representation of the short-term power spectrum of sound, based on a linear cosine transform of a log power spectrum on a nonlinear mel scale of frequency. MFCCs are derived from a type of cepstral representation of an audio sample. The frequency bands of an MFC are equally spaced on the mel scale, which approximates the human auditory system's response more closely than linearly-spaced frequency bands used in the conventional cestrum. In some implementations, MFCCs are derived by: (1) Compute the Fourier transform of a windowed excerpt of a signal; (2) Map the powers of the spectrum resulting from the Fourier transform onto the mel scale, using triangular (or other shapes) overlapping windows; (3) Compute the logs of the powers at each of the mel frequencies; (4) compute the discrete cosine transform of the list of mel log powers; (5) determine the MFCCs, which are represented as the amplitudes of the resulting spectrum. In some implementations, only the first 12 to 20 MFCCs are determined for a given time interval. In some implementations, 13 MFCCs are determined for a given time interval. However, more or less MFCCs can be determined based on efficiency considerations and data available. When converting to MFCCs, information of timing (e.g., which frequencies occur before another) may be lost.

In some implementations, the plurality of discrete values include continuous differences in wavelength of the raw audio sample converted into sound intensity values. Sound intensity values refer to the power carried by sound waves per unit area in a direction perpendicular to that area. In some implementations, the plurality of discrete values include spectral centroid values. Spectral centroid values indicate the location of the "center of mass" of a spectrum (e.g., an audio sample). Spectral centroid values can be calculated as the weighted mean of the frequencies present in a given signal, determined using a Fourier transform, with the frequencies' magnitude as the weights. In some implementations, the plurality of discrete values include spread values. A spread value refers to the width of distribution of different frequencies for a given time series.

In some implementations, the plurality of discrete data elements include skewness values. Skewness values indicate the symmetry of the probability density function of the amplitude of a time series. For example, an audio sample with an equal number of large and small amplitude values can have a skewness value of zero. An audio sample with an equal number with many small amplitude values and few large amplitude values can have a positive skewness value. An audio sample with many large amplitude values and few small amplitude values can have a negative skewness value. In some implementations, the plurality of discrete values includes a kurtosis value. A kurtosis value measures the "peakedness" of the probability density function of an audio sample. For example, a kurtosis value close to three can indicate a Gaussian-like "peakedness." Kurtosis values greater than three can indicate sharp peaks, while kurtosis values less than three can indicate relatively flat peaks. In some implementations, the plurality of discrete date elements include decrease values. A decrease value refers to the difference between the highest and lowest frequencies of a given time series.

In some implementations, the plurality of discrete data elements includes spectral slope values. For example, a linear regression can be applied to the Fourier magnitude spectrum of the audio data to produce a single number indicating the slope of the line-of-best-fit through the spectral data. This number can indicate the tendency of the natural audio signal to have less energy at high frequencies. In some implementations, the plurality of discrete data elements include rolloff values. Rolloff refers to the frequency below which approximately 85% of the magnitude distribution of the raw audio data spectrum is concentrated. Typically, rolloff is a measure of spectral shape and higher rolloff values tend to correspond to higher frequencies.

The plurality of discrete data elements generated by the computer processors 110 can include one or more of the aforementioned discrete data elements. In some implementations, the computer processors 110 generate at least two of the aforementioned discrete data elements for a given audio sample (e.g., MFCC and Centroid). However, the computer processors 110 can generate more discrete data elements. The amount of discrete data elements generated can be a user selection or a manufacturer's design choice and be based on computational considerations and practical needs.

When the computer processors 110 execute the computer-executable instructions 112, the computer processors 110 are configured to store, in memory (e.g., computer-readable medium 111), the generated plurality of discrete data elements for the predetermined time interval.

Converting the captured raw audio data to discrete data elements can allow for a creation of a unique audio signature of an environment without collecting any discernable sound. Although the system 100 as shown in FIG. 1 is deployed in a medical environment 101, the system 100 can be deployed in a variety of environments. For example, the system 100 can be employed in government facilities (e.g., the department of motor vehicles) and restaurants (e.g., fast food restaurants, sit-down restaurants, nightclubs, etc.) to capture acoustic fingerprints of these establishments during working hours. These acoustic fingerprints can be used to associate sound with performance outcomes without breaching the privacy of the people within the environment.

In some implementations, the computer processors 110 are trained to identify a pattern of the plurality of discrete data elements and determine at least one characteristic of an environment based on the identified pattern. For example, using one or more machine learning techniques (e.g., Bayesian learning, deep learning, etc.), the computer processors 110 can predict whether or not an environment is a "good environment" or a "bad environment" based on the acoustic fingerprints of the environment (e.g., by identifying a patterns presented by the plurality of discrete elements of the acoustic fingerprints). A "good environment" can be an environment in which employees are operating efficiently, customers/patients are being treated respectfully, managers are treating employee staff respectfully, there is low risk of customer/patient safety issues, and so forth. A "bad environment" can be an environment in which employees are not operating efficiently, customers/patients are not being treated respectfully, managers are not treating employee staff respectfully, and so forth. The computer processors 110 can be trained to associate certain patterns of the discrete data elements, such as, for example, certain MFCCs and intensity values, with a "good environment" and/or a "bad environment" and classify the environment accordingly. Based on these classifications and the acoustic fingerprints, the computer processors 110 can also determine how much assistance, advanced education, and or training a "bad environment" requires to become a "good environment." Furthermore, in some implementations, the computer processors 110 are configured to predict one or more performance outcomes associated with the environment. For example, a "good environment" can objectively result in higher customer satisfaction, increased profits, lower employee turnover, and so forth. On the other hand, a "bad environment" can objectively result in lower customer satisfaction, lower profits, and higher employee turnover when compared to a "good environment." Consequently, based on the acoustic fingerprints of the environment, the computer processors 110, when trained to associate outcomes with the aforementioned discrete data elements, can predict performance outcomes of the environment such as employee turnover rate, customer/patient satisfaction, and/or profit amounts.

In some implementations, the computer processors 110 are capable of predicting one or more patient outcomes related to the quality of care of an environment based on the acoustic fingerprint. For example, the computer processors 110 can predict the overall satisfaction of patients regarding the services of a clinic and/or the likelihood that a patient will return to the clinic for similar treatments. In some implementations, the computer processors 110 are capable of predicting a number and/or type of regulatory citation an environment might receive based on the acoustic fingerprints. For example, the computer processors 110 can predict that a restaurant will receive a food safety citation or that a clinic will receive a safety citation based on the acoustic fingerprints.

While the system 100 is described as being used to determine characteristics of an environment 101 and/or patient outcomes based on the identified pattern of the plurality of discrete data elements, the system 100 can be used in other scenarios. For example, the system 100 can be used to convert sound data associated with various heart sounds and/or arteriovenous (AV) fistula generated thrill/bruit (e.g., rumblings resulting from blood flow through the AV fistula) to discrete data elements. Further, based on identifying certain patterns in the discrete data elements, the system 100 can learn to determine if the patterns indicate cardiac abnormalities.

While the system 100 is described as being used to convert continuous audio data to discrete data values, in some implementations, the system 100 is used to convert other types of data. For example, the system 100 can include an image capture device (e.g., camera) for capturing image data during, for example, a physical evaluation of a patient. The system 100 can then convert this image data to discrete data values and determine certain medical conditions (e.g., bone fractures, joint dislocations, etc.) based on the discrete data values. The system 100 can include a pressure sensor that can, for example, be placed on a patient's body to capture pressure information. This pressure information can be converted to discrete data values to determine certain medical conditions of the patient, such as if the patient has peripheral edema or an appropriate access thrill when using a an arteriovenous fistula. In some implementations, the system 100 can be used to convert several types of data (e.g., pressure, visual, audio) to discrete data values. Accordingly, the system 100 can be used to convert human senses, such as hearing, vision, and pressure (touch) to discrete data values for the application of machine learning to facilitate the delivery of personalized care to patients (e.g., by obtaining unique signatures of dialysis patients).

Figure 2:
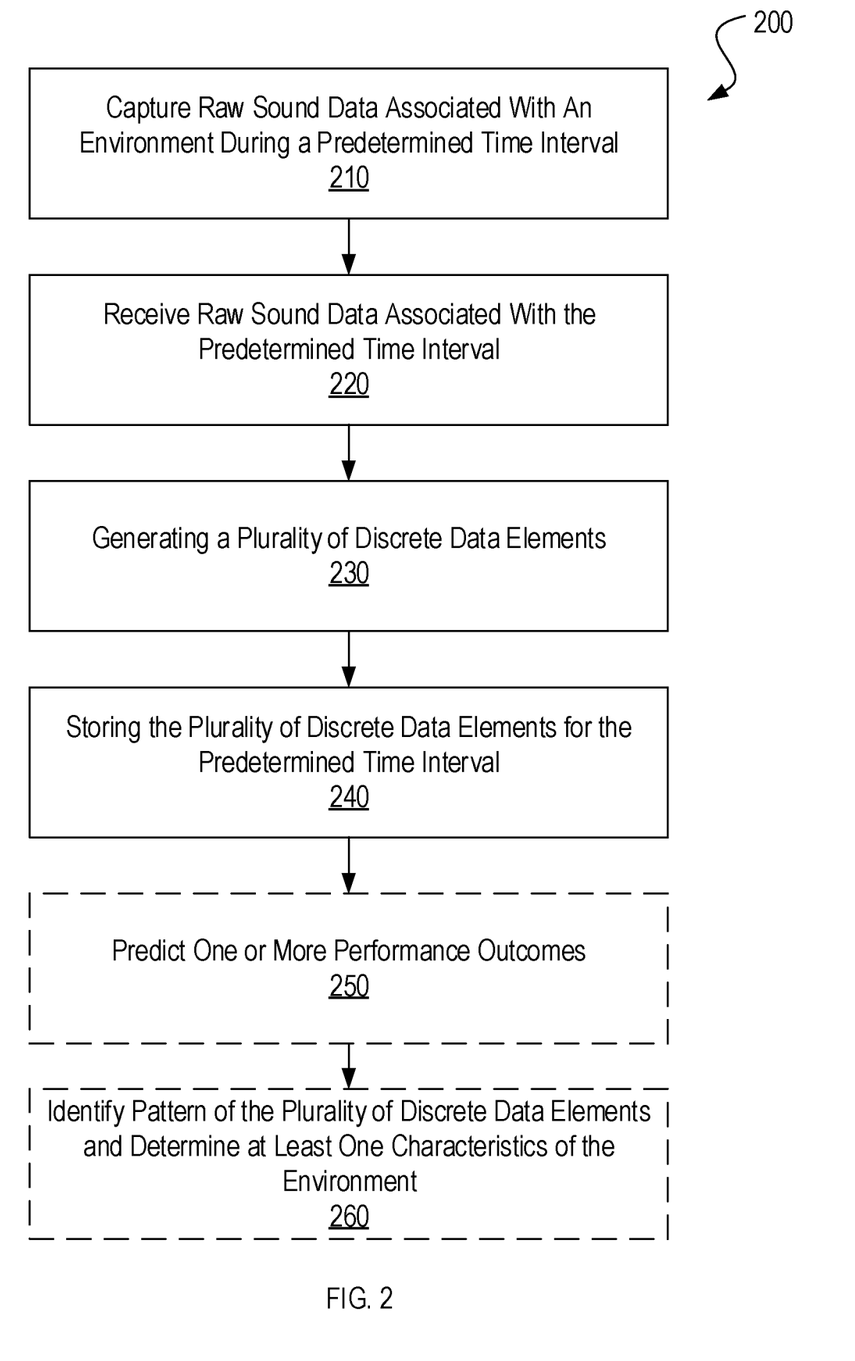
FIG. 2 shows a flowchart depicting an example of a method for generating an anonymized acoustic fingerprint for an environment.

FIG. 2 shows a flowchart depicting an example of a method 200 for generating an anonymized acoustic fingerprint for an environment. For illustrative purposes, the method 200 is described as being performed by the system 100 for generating an anonymized acoustic fingerprint for an environment and described previously with reference to FIG. 1. The method 200 includes capturing raw sound data associated with an environment during a predetermined time interval (block 210), receiving raw sound data associated with the predetermined time interval (block 220), generating a plurality of discrete data elements (block 230), and storing the plurality of discrete data elements for the predetermined time interval (block 240). In some implementations, the method 200 includes predicting one or more performance outcome (block 250). In some implementations, the method 200 includes identifying a pattern of the plurality of discrete data elements and determining at least one characteristics of the environment (block 260).

At block 210, the one or more acoustic sensors 120 are caused by the computer processors 110 to begin capturing the raw sound data for a predetermined time interval. The computer processors 110 cause the one or more acoustic sensors to stop capturing raw sound data at the end of the predetermined time interval (e.g., an audio sample/time series). In some implementations, the predetermined time interval is greater than 5 seconds. In some implementations, the predetermined time interval is greater than 10 seconds. The predetermine time interval can be user selected and/or a manufacturing design choice and be based on computational power, efficiency, and data storage considerations.

At block 220, the computer processors 110 receive, from the one or more acoustic sensors 120, raw sound data associated with the environment for the predetermined time interval. For example, the one or more acoustic sensors 120 can capture soundwaves, convert the soundwaves into raw usable data (e.g., electronic energy), amplify the raw usable data with a preamplifier, and send the amplified raw usable data to the computer processors 110.

At block 230, the computer processors 110 generate, based on the received raw sound data, a plurality of discrete data elements. In some implementations, the plurality of discrete data elements include one or more intensity values, one or more centroid values, one or more spread values, one or more skewness values, one or more kurtosis values, one or more decrease values and/or one or more Mel-frequency cepstral coefficients.

At block 240, the computer processors store the plurality of discrete data elements generated for a predetermined time interval in memory. In some implementations, the discrete data elements are stored in the computer-readable medium 111.

At block 250, the computer processors 110 predict one or more performance outcomes associated with the environment. For example, based on the generated discrete data elements, the computer processors 110 can predict performance outcomes of the environment such as employee turnover rate, customer/patient satisfaction, and/or profit amounts. At block 260, the computer processors 110, using one or more machine learning techniques (e.g., Bayesian learning, deep learning, etc.), predict whether or not an environment is a "good environment" or a "bad environment" based on the acoustic fingerprints of the environment (e.g., by identifying a patterns presented by the plurality of discrete elements of the acoustic fingerprints). The computer processors 110 can be trained to associate certain patterns of the discrete data elements, such as, for example, certain MFCCs and intensity values, with a "good environment" and/or a "bad environment" and classify the environment accordingly.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

Experimental Results

In an example experiment, a system for generating an anonymized acoustic fingerprint was placed inside a dialysis clinic. The acoustic sensor was installed in the clinic for a period of 24 hours. The system collected numeric data reflecting the acoustic fingerprint of the clinic every 10 minutes, in 10 second intervals. The system generated 21 discrete data values, including volume values, centroid values, slope values, spread values, skewness values, kurtosis values, decrease values, rolloff values, and 13 mel-frequency cepstral coefficients.

Figure 3:
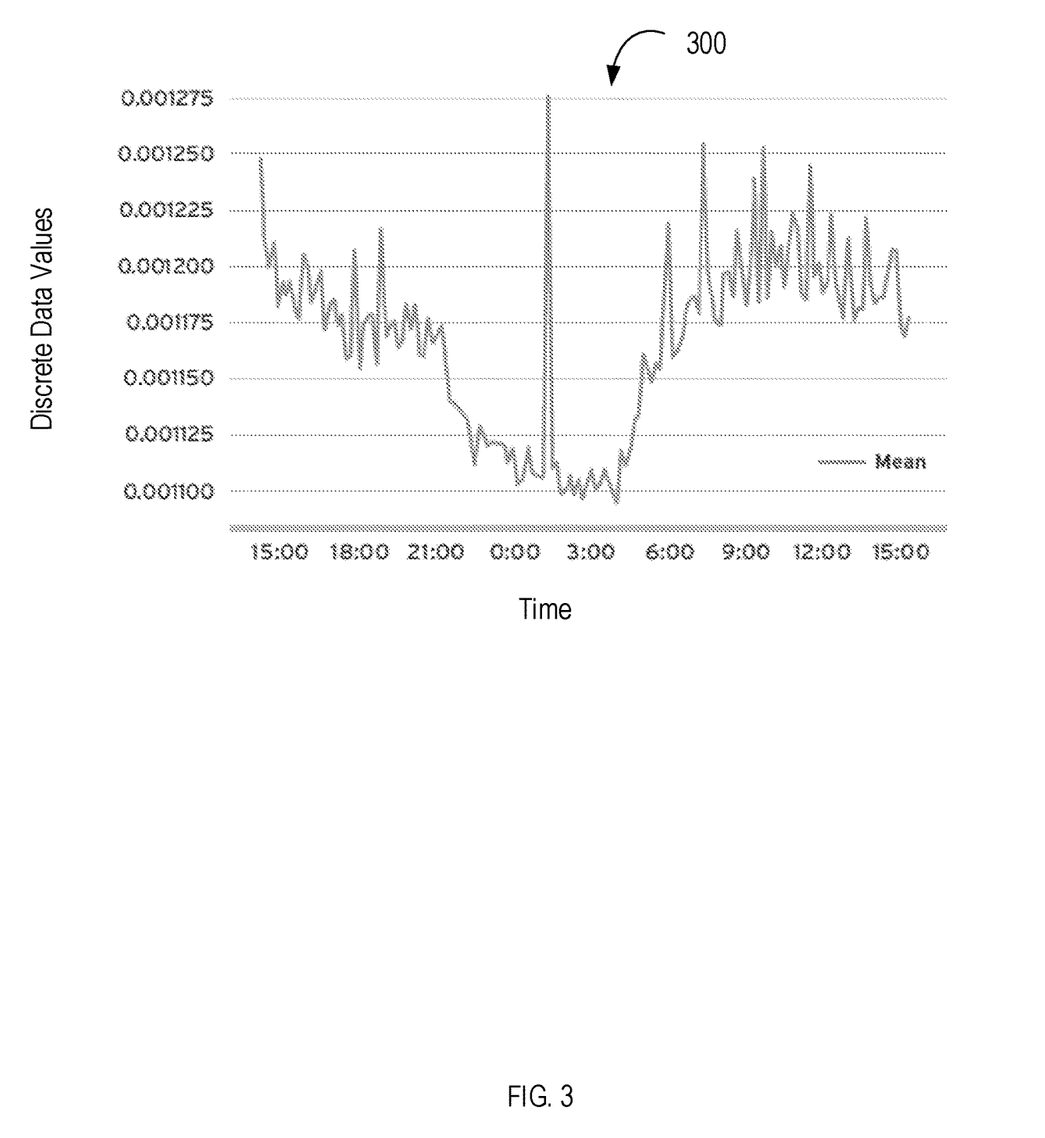
FIG. 3 shows an acoustic fingerprint detected for a dialysis clinic.

FIG. 3 shows an example of the acoustic fingerprint 300 detected for the clinic. Using the acoustic fingerprint 300 of the clinic and a machine learning algorithm (e.g., XGBoost), a data analysis technique predicted when patients would leave their dialysis chairs. Several factors were determined to be important in making these predictions, such as changes in the centroid function of the frequency and the mel-frequency cepstral coefficients 0, 1, 4, 7, and 8. Therefore, it was shown that these discrete data values can be used to predict certain outcomes associated with an environment, such as when a patient would leave their dialysis chair in a dialysis clinic.

Example Computer System

Figure 4:
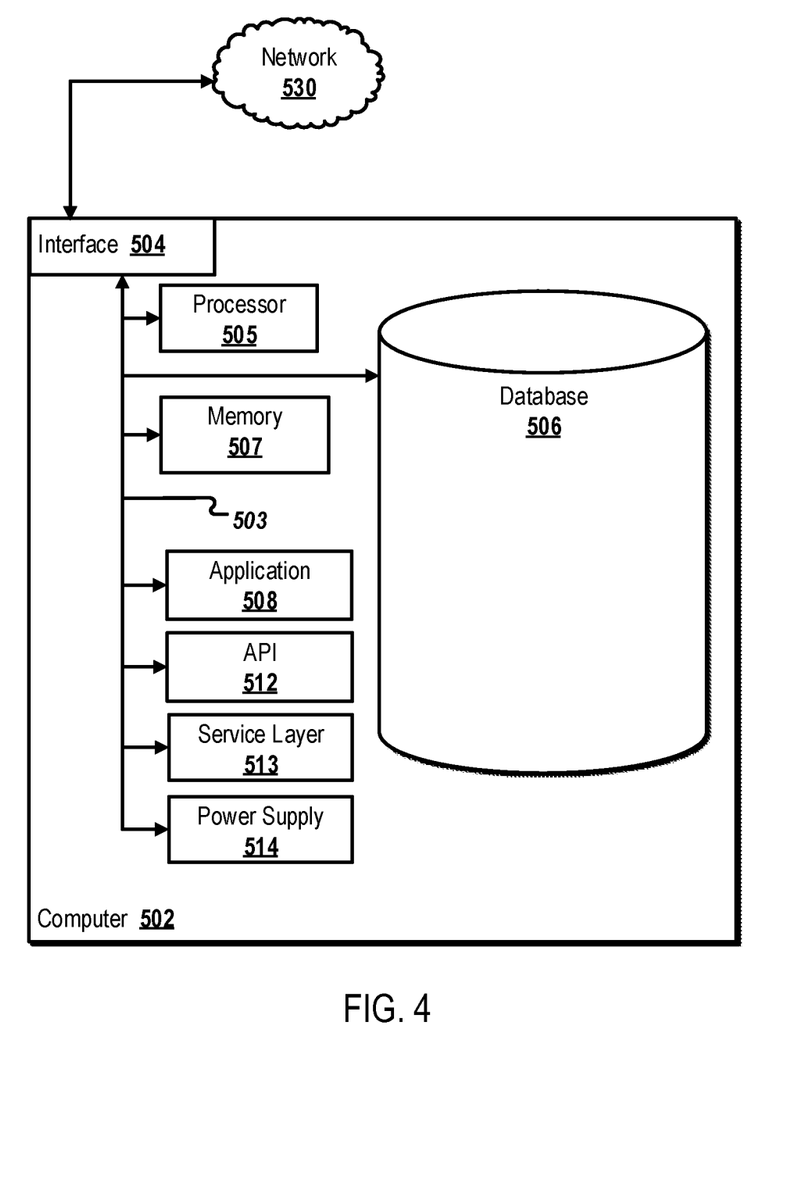
FIG. 4 is a block diagram of an example computer system used to provide computational functionalities associated with described algorithms, methods, functions, processes, flows, and procedures described in the present disclosure.

FIG. 4 is a block diagram of an example computer system 500 used to provide computational functionalities associated with described algorithms, methods, functions, processes, flows, and procedures described in the present disclosure (such as the method 200 described previously with reference to FIG. 2), according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a high level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 504 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 4, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the interface's hardware can be operable to communicate physical signals within and outside of the illustrated computer 502.

The computer 502 includes a processor 505. Although illustrated as a single processor 505 in FIG. 4, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 4, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 4, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "computer processors," "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A method of generating an anonymized acoustic fingerprint for a dialysis environment, the method comprising:
   capturing, using at least one acoustic sensor, raw ambient sound data associated with the dialysis environment during a predetermined time interval, the raw ambient sound data comprising audio data associated with at least one of medical personnel, a patient, or a dialysis machine in the dialysis environment;
   processing the captured raw ambient sound data to convert the raw ambient sound data into a plurality of discrete data elements, wherein the plurality of discrete data elements are indicative of acoustic characteristics of the dialysis environment that cannot be converted back to identifiable ambient sounds of the raw ambient sound data associated with the at least one of the medical personnel, the patient, or the dialysis machine;

storing, in memory, the plurality of discrete data elements for the predetermined time interval without storing any audio information comprising identifiable ambient sounds;

identifying a pattern of the plurality of discrete data elements;

classifying, based on the identified pattern, the dialysis environment as a good environment or a bad environment; and in response to classifying the dialysis environment as a bad environment, determining, based on the plurality of discrete data elements, assistance, education or training required for the dialysis environment to be converted to a good environment.

2. The method of claim 1, wherein the acoustic characteristics comprise at least one of: an intensity value, a centroid value, a spread value, a skewness value, a kurtosis value, a decrease value, a rolloff value, a spectral slope value, or a mel-frequency cepstral coefficient.

3. The method of claim 1, wherein the predetermined time interval is greater than 5 seconds.

4. The method of claim 1, further comprising predicting, based on the acoustic characteristics, one or more performance outcomes associated with the dialysis environment.

5. The method of claim 4, wherein the one or more performance outcomes comprises patient satisfaction.

6. The method of claim 1, wherein:
the raw ambient sound data comprises sound generated by at least one of: a heart or arteriovenous fistula thrill; and
the method further comprises determining, based on the plurality of discrete data elements, a medical condition of the patient in the dialysis environment.

7. The method of claim 1, wherein the at least one acoustic sensor comprises a microphone.

8. The method of claim 1, wherein classifying, based on the identified pattern, the dialysis environment as a good environment or a bad environment comprises:
identifying, based on the identified pattern, at least one condition of the dialysis environment, the at least one condition comprising employees in the dialysis environment operating efficiently, persons in the dialysis environment are being treated respectfully, or there existing a low risk of safety issues; and
in response to identifying the at least one condition of the dialysis environment, classifying the dialysis environment as a good environment.

9. The method of claim 1, further comprising predicting, based on the plurality of discrete data elements, when a patient in the dialysis environment will leave a dialysis chair in the dialysis environment.

10. The method of claim 1, further comprising:
capturing, using at least one sensor, raw pressure data associated with the dialysis environment during a predetermined time interval;
processing the captured raw pressure data to convert the raw pressure data into a second plurality of discrete data elements; and
storing, in memory, the second plurality of discrete data elements for the predetermined time interval.

11. The method of claim 1, wherein the audio data comprises an audible interaction between the patient and the medical personnel.

12. The method of claim 1, wherein the audio data comprises an audible alert or an operational noise associated with the dialysis machine.

13. A system, comprising:
at least one acoustic sensor configured to capture raw sound data associated with a dialysis environment;
a computer-readable medium comprising computer-executable instructions; and
one or more processors configured to execute the computer-executable instructions,
wherein, when the one or more processors are executing the computer-executable instructions, the one or more processors are configured to carry out operations comprising:
receiving, from the at least one acoustic sensor, raw ambient sound data associated with the dialysis environment during a predetermined time interval, the raw ambient sound data comprising audio data associated with at least one of medical personnel, a patient, or a dialysis machine in the dialysis environment;
processing the received raw ambient sound data to convert the raw ambient sound data into a plurality of discrete data elements, wherein the plurality of discrete data elements are indicative of acoustic characteristics of the dialysis environment that cannot be converted back to identifiable ambient sounds of the raw ambient sound data associated with the at least one of the medical personnel, the patient, or the dialysis machine;
storing, in memory, the plurality of discrete data elements for the predetermined time interval without storing any audio information comprising identifiable ambient sounds;
identifying a pattern of the plurality of discrete data elements;
classifying, based on the identified pattern, the dialysis environment as a good environment or a bad environment; and
in response to classifying the dialysis environment as a bad environment, determining, based on the plurality of discrete data elements, assistance, education or training required for the dialysis environment to be converted to a good environment.

14. The system of claim 13, wherein the plurality of discrete data elements comprises at least one of: an intensity value, a centroid value, a spread value, a skewness value, a kurtosis value, a decrease value, a rolloff value, a spectral slope value, or a mel-frequency cepstral coefficient.

15. The system of claim 13, wherein the predetermined time interval is greater than 5 seconds.

16. The system of claim 13, wherein the at least one acoustic sensor comprises a microphone.

17. The system of claim 13, wherein, when the one or more processors are executing the computer-executable instructions, the one or more processors are further configured to carry out operations comprising predicting, based on the plurality of discrete data elements, one or more performance outcomes associated with the dialysis environment.

18. The system of claim 13, wherein:
the raw ambient sound data comprises sound generated by at least one of: a heart or arteriovenous fistula thrill; and
the operations further comprise determining, based on the plurality of discrete data elements, a medical condition of a patient in the dialysis environment.

19. A non-transitory computer-readable storage medium having instructions executable by one or more processors to cause the processors to perform operations comprising:
capturing, using at least one acoustic sensor, raw ambient sound data associated with a dialysis environment during a predetermined time interval, the raw ambient sound data comprising audio data associated with at least one of medical personnel, a patient, or a dialysis machine in the dialysis environment;

processing the captured raw ambient sound data to convert the raw ambient sound data into a plurality of discrete data elements, wherein the plurality of discrete data elements are indicative of acoustic characteristics of the dialysis environment that cannot be converted back to identifiable ambient sounds of the raw ambient sound data associated with the at least one of the medical personnel, the patient, or the dialysis machine;

storing, in memory, the plurality of discrete data elements for the predetermined time interval without storing any audio information comprising identifiable sounds;

identifying a pattern of the plurality of discrete data elements;

classifying, based on the identified pattern, the dialysis environment as a good environment or a bad environment; and in response to classifying the dialysis environment as a bad environment, determining, based on the plurality of discrete data elements, assistance, education or training required for the dialysis environment to be converted to a good environment.

20. The non-transitory computer-readable storage medium of claim 19, wherein the plurality of discrete data elements comprises at least one of: an intensity value, a centroid value, a spread value, a skewness value, a kurtosis value, a decrease value, a rolloff value, a spectral slope value, or a mel-frequency cepstral coefficient.

21. The non-transitory computer-readable storage medium of claim 19, wherein the predetermined time interval is greater than 5 seconds.

22. The non-transitory computer-readable storage medium of claim 19, the operations further comprising predicting, based on the plurality of discrete data elements, one or more performance outcomes associated with the dialysis environment.

23. The non-transitory computer-readable storage medium claim 19, wherein:
the raw ambient sound data comprises sound generated by at least one of: a heart or arteriovenous fistula thrill; and
the operations further comprise determining, based on the plurality of discrete data elements, a medical condition of a patient in the dialysis environment.

24. The non-transitory computer-readable storage medium of claim 19, wherein the at least one acoustic sensor comprises a microphone.

* * * * *

UNITED STATES PATENT AND TRADEMARK OFFICE
CERTIFICATE OF CORRECTION

PATENT NO. : 12,315,530 B2
APPLICATION NO. : 16/748115
DATED : May 27, 2025
INVENTOR(S) : Len Usvyat et al.

Page 1 of 1

It is certified that error appears in the above-identified patent and that said Letters Patent is hereby corrected as shown below:

In the Claims

<u>Claim 23</u>
Column 20, Line 15, after "medium" insert --of--.

Signed and Sealed this
Twenty-second Day of July, 2025

Coke Morgan Stewart
*Acting Director of the United States Patent and Trademark Office*